United States Patent [19]
Ochoa et al.

[11] Patent Number: 5,296,353
[45] Date of Patent: Mar. 22, 1994

[54] EVALUATION AND TREATMENT OF PATIENTS WITH PROGESSIVE IMMUNOSUPPRESSION

[75] Inventors: Augusto C. Ochoa, Washington, D.C.; Hiromoto Mizoguchi, Frederick, Md.; John J. O'Shea, Silver Spring, Md.; Dan L. Longo, Kensington, Md.; Cynthia M. Loeffler, Bladensburg, Md.

[73] Assignees: The United States of America as represented by the Department of Health and Human Services, Washington, D.C.; Regents of the University of Minnesota, Minneapolis, Minn.

[21] Appl. No.: 863,262

[22] Filed: Apr. 6, 1992

[51] Int. Cl.$^5$ .................. G01N 33/573; G01N 33/574
[52] U.S. Cl. ............................ 435/7.23; 424/93 V; 424/534; 435/7.24; 435/7.4; 435/15; 435/29; 436/63; 436/64; 436/86
[58] Field of Search .................. 435/7.23, 7.24, 29, 435/15, 7.4; 424/534, 93 V; 436/86, 63, 64

[56] References Cited

U.S. PATENT DOCUMENTS

| | | |
|---|---|---|
| 4,690,915 | 9/1987 | Rosenberg .......................... 514/2 |
| 5,024,940 | 6/1991 | Brenner et al. ................... 435/69.1 |
| 5,124,251 | 6/1992 | Lanier et al. ..................... 435/7.21 |

OTHER PUBLICATIONS

M. Furue et al, *J. Immunol.*, 144, 736–739, 1990.
Irving et al., "The Cytoplasmic Domain of the T Cell Receptor ξ Chain is Sufficient to Couple to Receptor-Asociated Signal Transduction Pathways" (Mar. 1991) *Cell* 64: 891–901.
Letourneur et al., "Activation of T Cells by a Tyrosine Kinase Activation Domain in the Cytoplasmic Tail of CD3 ε" (Jan. 1992) *Science* 255: 79–82.
Klausner et al., "T Cell Antigen Receptor Activation Pathways: The Tyrosine Kinase Connection" (Mar. 1991) *Cell* 64: 875–878.
Smyth et al., "Regulation of Lymphokine-Activation Killer Activated Killer Activity and Pore-Forming Protein Gene Expression in Human Peripheral Blood CD8+ T Lymphocytes" *Immunol.* 146: 3289–3297.
Schmitt-Verhulst et al., "Pleiotropic loss of activation in a T-cell receptor α-chain delection variant of a cytolytic T-cell clone" *Nature* 325: 628–631.
Buferne et al., "Role of CD3δ in Surface Expression of the TCR/CD3 Complex and in Activation for Killing Analyzed with a CD3δ-Negative Cytotoxic T Lymphocyte Variant" *J. Immunol.* 148: 657–664.
Klausner et al., "The T Cell Antigen Receptor: Insights into Organelle Biology" *Annu. Rev. Cell Biol.* 6: 403–431.
Blumberg, et al., "Structure of the T-cell antigen receptor: Evidence for two CD3 ε subunits in the T-cell receptor-CD3 complex" (Sep. 1990) *Proc. Natl. Acad. Sci. USA* 87: 7220–7224.
Patel et al., "Multiple Kinases and Signal Transduction" (Apr. 1987) *J. Biol. Chem.* 262: 5831–5838.
Samelson et al., "Antigen Activation of Murine T Cells Induces Tyrosine Phosphorylation of a Polypeptide Associated with the T Cell Antigen Receptor" (Sep. 1986) *Cell* 46: 1083–1090.
Hsi et al., "T Cell Activation Induces Rapid Tyrosine Phosphorylation of a Limited Number of Cellular Substrates" (Jun. 1989). *J. Biol. Chem.* 264: 10836–10842.
June et al., "Increases in Tyrosine Phosphorylation are Detectable before Phospholipase C Activation After T Cell Receptor Stimulation" (Mar. 1990). *J. Immunol.* 144: 1591–1599.

(List continued on next page.)

*Primary Examiner*—David Saunders
*Attorney, Agent, or Firm*—Foley & Lardner

[57] ABSTRACT

A method of determining the level of immunosuppression in a mammal involves determining the level of expression of at least one selected TCR subunit protein, or protein in the T lymphocyte signal transduction pathway, and comparing the level to that found in healthy individuals. The method is useful to identify patients having T lymphocytes capable of activation for autologous adoptive immunotherapy and for identifying agents which cause or reverse immunosuppression.

6 Claims, 3 Drawing Sheets

OTHER PUBLICATIONS

Loeffler et al., "Immunosuppression in Tumor Bearing Mice: Function and Molecular Basis" (Mar. 1991) First International Symposium on Combination Therapies, George Washington School of Medicine, Abstract No. 6.

Samelson et al, "Association of the fyn protein-tyrosine kinase with the T-cell antigen receptor" (Jun. 1990) *Proc. Natl. Acad. Sci. USA* 87:4358-4362.

Weiss et al., "Role of T3 surface molecules in human T-cell activation: T3-dependent activation results in an increase in cytoplasmic free calcium" (Jul. 1984) *Proc. Natl. Acad. Sci. USA* 81: 4169-4173.

Imboden et al., "Transmembrane Signalling by the T Cell Antigen Receptor" (Mar. 1985) *J. Exp. Med.* 161: 446-456.

Ullman et al., "Transmission of Signals from the T Lymphocyte Antigen Receptor to the Genes Responsible for Cell Proliferation and Immune Function: The Missing Link" (1990) *Ann. Rev. Immunol.* 8: 421-452.

Weiss et al., "The Role of the T3/Antigen Receptor Complex in T-Cell Activation" (1986) *Ann. Rev. Immunol.* 4: 593-619.

Frank et al., "Structural Mutations of the T Cell Receptor $\xi$ Chain and its Role in T Cell Activation" *Science*, 249: 174-177.

Rodewald et al., "The High Affinity Fc$\epsilon$e Receptor $\gamma$ Subunit (Fc$\epsilon$Rl$\gamma$) Facilitates T Cell Receptor Expression and Antigen/Major Histocompatibility Complex-driven Signaling in the Absence of CD3$\xi$ and CD3$\eta$" (Aug. 1991) *J. Biol. Chem.* 266: 15974-15978.

Hommel-Berrey et al., "Receptor Modulation and Early Signal Transduction Events in Cytotoxic T Lymphocytes Inactivated by Sensitive Target Cells" (Nov. 1991) *J. Imunol.* 147: 3237-3243.

Sussman et al., "Failure to Synthessize the T Cell CD3-$\xi$ Chain: Structure and Function of a Partial T Cell Receptor Complex" (Jan. 1988) *Cell* 52: 85-95.

Chan et al., "The $\xi$ chain is associated with a tyrosine kinase and upon T-cell antigen receptor stimulation associates with ZAP-70, a 70-kDa tyrosine phosphoprotein" (Oct. 1991) *Proc. Natl. Acad. Sci. USA* 88: 9166-9170.

Weissman et al, "Role of the zeta chain in the expression of the T cell antigen receptor: genetic reconstitution studies" (1989) *EMBO J.* 8: 3651-3656.

Weissman et al., "Tyrosine Phosphorylation of the Human T Cell Antigen Receptor $\xi$-chain: Activation via CD3 but not CD2" (Nov. 1988) *J. Immunol.* 141: 3562-3536.

Baniyash et al., "The T Cell Antigen Receptor $\xi$ Chain is Tyrosine Phosphorylated upon Activation" (Dec. 1988) *J. Biol. Chem.* 263: 18225-18230.

Wegener et al., "The T Cell Receptor.CD3 Complex is Composed of at Least Two Autonomous Transduction Modules" (Jan. 1992) *Cell* 68: 83-95.

EVALUATION AND TREATMENT OF PATIENTS WITH PROGESSIVE IMMUNOSUPPRESSION

FIELD OF THE INVENTION

The present invention relates to the evaluation, selection and treatment of patients with diseases causing progressive immunosuppression. Patients having a disease responsive to autologous adoptive immunotherapy, especially cancer patients, can be staged and evaluated as to the likelihood of success of such therapy. Immunosuppressive agents and counter-agents can be recognized using the invention.

BACKGROUND OF THE INVENTION

Many diseases are characterized by the development of progressive immunosuppression in the patient. The presence of an impaired immune response in patients with malignancies has been particularly well documented. Cancer patients and tumor-bearing mice have been shown to have a variety of altered immune functions such as a decrease in delayed type hypersensitivity, a decrease in lytic function and decreased proliferative response. S. Broder et. al., *N. Engl. J. Med.*, 299, 1281 (1978), E. M. Hersh et. al., *N. Eng. J. Med.*, 283, 1006 (1965).

Many other diseases are also characterized by the development of an impaired immune response. Progressive immunosuppression has been observed in patients with acquired immunodeficiency syndrome (AIDS), sepsis, leprosy, cytomegalovirus infections, malaria, etc. The mechanisms responsible for the down-regulation of the immune response, however, remain to be elucidated.

T lymphocytes (T cells) are critical in the development of all cell-mediated immune reactions. Helper T cells control and modulate the development of immune responses. Cytotoxic T cells (killer T-cells) are effector cells which play an important role in immune reactions against intracellular parasites and viruses by means of lysing infected target cells. Cytotoxic T cells have also been implicated in protecting the body from developing cancers through an immune surveillance mechanism. T suppressor cells block the induction and/or activity of T helper cells. T cells do not generally recognize free antigen but recognize it on the surface of other cells. These other cells may be specialized antigen-presenting cells capable of stimulating T cell division or may be virally-infected cells within the body that become a target for cytotoxic T cells.

Cytotoxic or suppressor T cells usually recognize antigen in association with class I Major Histocompatibility Complex (MHC) products which are expressed on all nucleated cells. Helper T cells, and most T cells which proliferate in response to antigen in vitro, recognize antigen in association with class II MHC products. Class II products are expressed mostly on antigen-presenting cells and on some lymphocytes. T cells can be also divided into two major subpopulations on the basis of their cell membrane glycoproteins as defined with monoclonal antibodies. The CD4+ subset which expresses a 62 kD glycoprotein usually recognize antigen in the context of class II antigens, whereas the CD8+ subset expresses a 76 kD glycoprotein and is restricted to recognizing antigen in the context of Class I MHC.

The CD4+ subset can be further subdivided into two functionally distinct groups. One group of cells positively influences the immune response of T cells and B cells. The second group of cells induces suppressor/cytotoxic functions in CD8+ cells.

The definitive T-cell marker is the T-cell antigen receptor (TCR). TCR-2 is a heterodimer of two disulfide-linked polypeptides ($\alpha$ and $\beta$) while TCR-1 is structurally similar but consists of $\gamma$ and $\delta$ polypeptides. Both TCR-1 and TCR-2 are associated with a complex of polypeptides which comprise the CD3 complex.

The TCR found on the surface of all T cells is composed of six or seven different subunits which can be divided into three distinct subgroups of proteins. R. D. Klausner et. al., *Annu. Rev. Cell Biol.*, 6, 403 (1990). One subgroup of proteins comprises the $\zeta$ family dimers. Three proteins, encoded by two genes, appear to comprise the $\zeta$ mily. These proteins are $\zeta$, its alternately spliced form, $\eta$, and the $\gamma$ chain of multisubunit Fc$\gamma$ receptors. The heterodimers $\alpha\beta$ or $\gamma\delta$ within the receptor complex are responsible for ligand binding. The heterodimer is found on most mature T cells and the $\alpha\beta$ heterodimer is found predominantly on T cells that are $\gamma\delta$ located in epithelia.

The final subgroup of proteins which comprise the TCR are the CD3 chains which encompass three distinct, but closely related subunits. These subunits are the glycoproteins $\gamma$ and $\delta$ and the non-glycosylated protein $\epsilon$. The CD3 chains are encoded by three homologous, clustered genes. F. Koning et. al., *Eur. J. Immunology*, 20, 299 (1990); R. S. Blumberg et. al., *Proc. Natl. Acad. Sci. USA*, 87, 7220 (1990). Diversification of receptor types is the result of segregation of chains of the TCR complex into multiple subunits. Incompletely assembled complexes are degraded, resulting in the surface expression of only completely assembled receptors. R. D. Klausner, *New Biol.*, 1, 3 (1989).

T-cell recognition events lead to signal transduction and appropriate biochemical signals that control cellular responses. The ability of TCR to transduce signals to multiple biochemical cascades is the central event of immune cell activation. The details of this signal transduction pathway, however, are poorly understood. For the TCR, one or more tyrosine (Tyr) kinases likely have an essential role in T-cell activation. R. D. Klausner et. al., *Cell.* 64. 875 (1991). At least two signal transduction pathways are activated upon stimulation of TCR by antigen or by monoclonal antibodies directed against CD3 or the $\alpha\beta$ heterodimer. Stimulation of TCR activates a tyrosine kinase. L. E. Samelson et. al., Cell 46, 1083 (1986); M. D. Patel et. al. *J. Biol.* 262, 5831 (1987); E. D. Hsi et. al., *J. Biol. Chem.* 264, 10836 (1989). Phosphorylation of several proteins on tyrosine residues is induced within seconds of TCR stimulation. C. H. June et. al., *J. Immunol.* 144, 1591 (1990). None of the TCR chains possesses intrinsic kinase activity. The tyrosine kinase Fyn, however, coprecipitates with the CD3 complex. L. E. Samelson et. al., *Proc Natl. Acad. Sci. USA.* 87, 4358 (1990). The T-cell-specific member of the Src family of tyrosine kinases, Lck, is tightly, but noncovalently, associated with the cytoplasmic domain of either the CD4 or CD8 molecule. The extracellular domains of CD4 and CD8 bind to MHC class II and class I molecules, respectively. Upon binding of TCR to an antigen-MHC complex on a presenting cell, the TCR would be brought into close proximity with either a CD4 or CD8 molecule that could independently bind to the appropriate MHC molecule.

TCR also activates a phosphatidylinositol-specific phospholipase C which leads to hydrolysis of phosphatidylinositol-4,5,-bis-phosphate. A. Weiss et. al., *Proc. Natl. Acad. Sci. USA.* 81, 4169 (1984); J. B. Imboden et. al., *J. Exp. Med.* 161, 446 (1985). This leads to the liberation of two second messengers. Inositol-1,4,5-tris-phosphate is responsible for transient $Ca^{+2}$ mobilization. Diacylglycerol is a potent activator of protein kinase C. B. Berridge et. al., *Nature*, 341, 197 (1989).

The cytoplasmic domain of the TCR ζ chain is sufficient to couple stimulation of the receptor with the signal transduction pathways. B. A. Irving et. al., *Cell.* 64, 891 (1991). A chimeric protein linking the extracellular and transmembrane domains of CD8 to the cytoplasmic domain of the ζ chain was constructed. The chimeric protein activated the appropriate signal transduction pathways in the absence of CD3 γ, δ, and ε. Therefore the role of CD3 ζ is to couple the TCR to intracellular signal transduction mechanisms.

The identification and isolation of soluble mediators of the immune response has heightened interest in the development of clinical trials using immunotherapy as a form of treatment. Interleukin-2 (IL-2), a lymphokine produced by helper T cells, stimulates the growth of T cells that bear IL-2 receptors, either in vivo or in vitro. The in vitro incubation of resting lymphocytes in supernatants containing IL-2 for three to four days results in the generation of lymphocytes capable of mediating the lysis of fresh tumor cells, but not normal cells. These cells are referred to as lymphokine activated killer (LAK) cells. I. Yron et. al., *J. Immunol.* 125. 238 (1980); M. T. Lotze et. al., *Cancer Res.* 41, 4420 (1981); and S. A. Rosenberg et. al., *J. Natl. Cancer Inst.*, 75, 595 (1985).

The activation of T lymphocytes to generate T-activated killer cells (T-AK) has been described as taking lymphocytes by leukophoresis or from peripheral blood, and stimulating said cells with a monoclonal antibody (MAb) to a T cell surface receptor such as anti-CD3 (soluble or solid phase bound). The T cells can be stimulated with or without addition of one or more cytokines such as IL-2. Alternatively, T cells can be purified before stimulation with the MAb to a surface receptor. Experimentation with T-AK cells has demonstrated that CD8+ cells are responsible for the non-MHC restricted cytolytic activity seen in these cultures. P. M. Anderson et. al., *J. Immunol.* 142. 1383 (1989); C. M. Loeffler et. al., *Cancer Res*, 51, 2127 (1991). The ability of IL-2 to expand T lymphocytes having immune reactivity and the ability to lyse fresh autologous, syngeneic, or allogeneic natural killer (NK) cell-resistant tumor cells, but not normal cells, has resulted in the development of cell transfer therapies.

Typical adoptive immunotherapy involves the administration of immunologically active cells to an individual for the purpose of providing a beneficial immunological effect such as reduction or control of cancer. These immunologically active cells are typically taken by venipuncture or leukophoreses either from the individual to be treated, as in autologous treatment, or from another individual, as in allogeneic treatment. The lymphocytes are then cultured to increase their number and to activate their antitumor activity, and then infused back into the patient. Thus, the majority of conventional efforts in adoptive immunotherapy are directed at expanding cells in vitro followed by infusion back into the patient.

Animal experiments involving the transfer of immunologically active cells from healthy animals to animals with cancerous tumors have indicated that adoptive immunotherapy can elicit an antitumor effect in certain tumor models with a high degree of effectiveness. The administration of IL-2 together with LAK cells has proven effective in the treatment of a variety of murine malignancies. The transferred LAK cells also proliferate in vivo as a result of IL-2 treatment. Human clinical trials have demonstrated that LAK cells plus IL-2 or IL-2 alone can be effective in mediating the regression of established metastatic cancer in selected patients. S. A. Rosenberg, "Immunotherapy of Patients with Advanced Cancer Using Interleukin-2 Alone or in Combination With Lymphokine Activated Killer Cells" in *Important Advances in Oncology* 1988, J. B. Lippincott Co., 217, (1988).

The success of adoptive immunotherapy has been limited by the large number of cells required in the therapy, the large amount of culture medium and large number of hours involved in culturing cells to develop LAK activity, the length of time sufficient LAK activity must be maintained for the desired therapeutic efficacy, the time involved in clinical treatment and the side effects of treatment. Improvements in the in vitro culturing process have been made in order to increase the efficacy of adoptive immunotherapy. Cells cultured in IL-2 and/or monoclonal antibodies against the antigen receptor complex CD3 (anti-CD3 MAb) have been found to induce proliferation of a greater number of T cells, which demonstrate an increased anti-tumor activity. P. M. Anderson et. al., *Cancer Immunol. Immunother.* 27, 82 (1988); P. M. Anderson et. al., *J. Immunol.* 142, 1383 (1989); and A. C. Ochoa et. al., *Cancer Res.* 49, 963 (1989).

There has been limited success with efforts to activate in vivo antitumor mechanisms. Only a minority of patients receiving high doses of IL-2 experienced therapeutic effects and significant toxicity is observed. The direct infusion of anti-CD3 monoclonal antibody alone induces nonspecific antitumor function in mice. D. W. Hoskin et. al., *Cancer Immunol Immunother.*, 29, 226 (1989). Based on the positive results in murine models, direct infusion of anti CD3 has been attempted in humans. Although patients who have directly received the anti-CD3 MAb OKT3 have experienced the activation of some T cells in vivo. The toxicity of intravenous OKT3 reaches the maximum tolerated dose (MTD) at low doses before it starts showing some immune efficacy. W. Urba et. al., *Cancer Res.*, in press. It is believed that the free OKT3 is responsible for the majority of these toxic effects.

T lymphocytes from hosts bearing tumors exhibit decreased immune function in a variety of in vitro tests. R. Lafreniere et. al., *J. Surg. Oncol.* 43, 8 (1990); R. J. North et. al., *J. Exc. Med.* 159, 1295 (1984); M. Sarzotti et. al., *Int. J. Cancer.* 39, 118 (1987). It has been observed that before the decrease in the immune responsiveness in peripheral blood lymphocytes, T lymphocytes infiltrating tumor exhibit poor cytotoxic activity against autologous or allogeneic tumor cells. E. F. Klein et. al., 1980, In: Contemporary Topics in Immunobiology, I. P. Witz and M. G. Hanna, Jr., eds. Plenum Press, N.Y., p 79–107; B. M. Vose et. al., *J. Cancer*, 44, 846 (1981).

The molecular basis of the decreased immune responsiveness of the T cells is poorly understood. It has been proposed that decreased immune responsiveness of the T cells is caused by the development of suppressor lymphocytes. S. B. Mizel et. al., *Proc. Natl. Acad. Sci. USA.* 77, 2205 (1980); C. C. Ting et. al., *Int. J. Cancer.* 4, 644 (1979). Another proposal is that responsive T-cell clones are deleted. S. Webb et. al., Cell. 63, 1249 (1990). It has also been proposed that decreased immune responsiveness of the T-cells is the result of the induction of T-cell energy. M. K. Jenkins et. al., *J. Exp. Med.* 165, 302 (1987). Others have suggested that the major alteration in the immune response is produced by a modification in the presentation of the antigen which results in an inadequate response of the CD4+ helper T lymphocytes. These data have been strengthened by the observation that tumor cells transfected with cytokine genes induce a protective antitumor response, and result in an immunological memory response. E. R. Fearon et. al., Cell. 60: 397 (1990).

Augmentation of the immune response in immune compromised patients via infusions of lymphokines and/or adoptive immunotherapy has met with variable success. In view of the fact that the immune system of the patient being treated may already be suppressed, a need exists for effective methods of measuring the progression of immunosuppression so that attempts at augmenting the immune system can be effectively timed. A need exists for a method by which the patient's level of immuno-suppression can be estimated and on the basis of which the patient's likely response to therapy can be predicted accurately and the patient's therapeutic plan can be developed. A method is needed by which the clinician can determine whether the patient's T lymphocytes will be capable of activation and, thus, whether autologous adoptive immunotherapy will likely be efficacious. A need exists for a method by which the immunosuppressed state of T lymphocytes during disease progression can be circumvented or reversed so that the T cell immune response in the patient can develop or be augmented. A need also continues to exist for a method of screening for immunosuppressive agents and agents that reverse or inhibit immunosuppression.

SUMMARY OF THE INVENTION

The foregoing objects can be achieved by providing, according to one aspect of the present invention, a method of identifying patients having T lymphocytes capable of activation for autologous adoptive immunotherapy, comprising the steps of determining, in a lymphocyte preparation from a patient being evaluated for immunosuppression, the level of expression of at least one selected TCR subunit protein or protein in the T lymphocyte signal transduction pathway, e.g., by determining the expression ratio, wherein the expression ratio is the ratio of the number of T lymphocytes expressing the selected protein to the total number of T lymphocytes counted; and comparing the level of protein expression with the normal level of expression of the selected protein found in healthy individuals, and selecting patients whose level of expression of the selected protein is at or above the threshold level for response to lymphocyte stimulation.

Application of the foregoing method to the treatment of patients having a disease responsive to autologous adoptive immunotherapy, permits selection of patients whose lymphocytes will respond to stimulation and for whom autologous adoptive immunotherapy is likely to succeed.

The foregoing are applications of a general method for determining the level of immunosuppression in a mammal, comprising the steps of determining the level of expression, in a mammalian lymphocyte preparation, of at least one selected TCR subunit protein or protein in the T lymphocyte signal transduction pathway; and comparing the level of protein expression with the normal level of expression of the selected protein found in healthy individuals of the same mammalian species.

Another aspect of the present invention relates to a method of selecting agents which cause immunosuppression of mammalian T lymphocytes, comprising the steps of: providing a mammalian T lymphocyte preparation wherein the level of expression of at least one selected TCR subunit protein or protein in the signal transduction pathway is normal compared to healthy individuals of the same mammalian species; culturing the lymphocyte preparation, in the presence of an agent suspected of causing immunosuppression; and determining the level of expression of the selected protein, and selecting for an agent which causes a significant reduction below normal in the level of expression of the selected protein.

Similarly, a method of identifying an agent which reverses immunosuppression of mammalian T lymphocytes, comprises the steps of: providing a mammalian T lymphocyte preparation from an immunosuppressed mammal, wherein the level of expression of at least one selected TCR subunit protein or protein in the signal transduction pathway is subnormal compared to healthy individuals of the same mammalian species; culturing the lymphocyte preparation, in the presence of an agent suspected of reversing immunosuppression; and determining the level of expression of the selected protein, and selecting for an agent which causes a significant increase in the level of expression of the selected protein.

Further objects, features and advantages of the invention will become apparent from the detailed description of the invention which follows.

DETAILED DESCRIPTION

Figure 1:
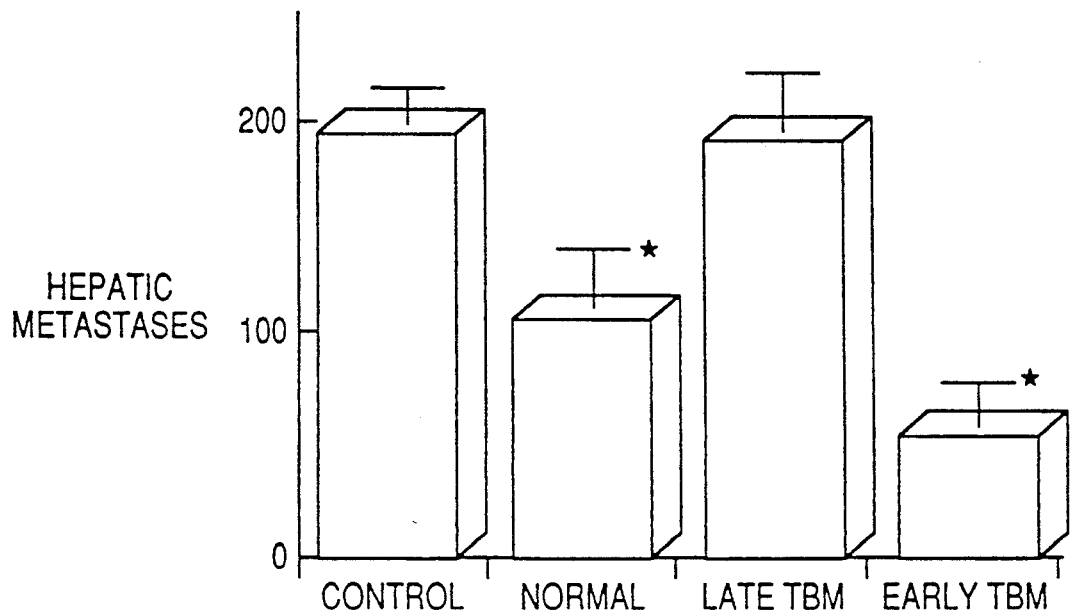
FIG. 1 illustrates the results of an experiment in which mice were treated with T-AK cells derived from non-tumor-bearing mice (normal) or mice bearing tumor for <21 days (early TBM) or >30 days (late TBM). Liver metastases were counted 12 days after tumor inoculation. Groups were compared using Student's unpaired t test. *, P<0.001 versus control. Bars, S. D.

As used herein "T lymphocytes" or "T cells" include all subsets of lymphocytes which carry the T cell antigen receptor. These subsets include lymphocytes which are CD3+CD4+($\alpha\beta$+); CD3+CD8+($\alpha\beta$+); CD3+CD4-CD8-($\gamma\delta$+); and CD3+CD56+.

As used herein, "adoptive immunotherapy" or "cellular adoptive immunotherapy" involves the administration of immunologically active (immunocompetent)

cells to an individual for the purpose of providing a beneficial immunological effect to the individual, such as reduction or control of cancerous or diseased tissue. As used herein, "immunotherapeutic activity" or "immune response" or "immunologically active" or "immunocompetent" includes anti-tumor activity, anti-infected cell activity, anti-disease agent activity and killer activity of white blood cells.

As used herein, "culturing" indicates the process whereby T cells are placed in a tissue culture medium (TCM) comprising all the nutrients required for growth. "Stimulating" indicates culturing the T cells in a TCM supplemented with one or more cytokines, or alternatively, with one or more T cell anti-surface receptor antibodies, with or without one or more cytokines. The process can take place in any vessel or apparatus. The process can involve various stages of culturing and subculturing. However, typically only one stimulating step is desirable.

As used herein, the "signal transduction pathway" includes any protein, the expression of which is induced, linked or regulated by the binding of a ligand or an antibody to any T cell surface receptor. These proteins include, but are not limited to, Jun, Fos, Myc, Yes, Lyn, Gap, Rafl, c-rel, NF$\kappa$B, Plc$\gamma$, Protein G, Inositol Phosphate, Protein Kinase C, Mapl kinase, the Src family of kinases including Lck and Fyn, and CD45 phosphatase.

As used herein, "antibody" includes any protein or protein analogue which binds specifically to an appropriate epitope of the T cell receptor that is stimulatory. Antibody also includes any protein or protein analogue which binds specifically to a TCR subunit protein, Fc$\epsilon\gamma$, or a protein in the T lymphocyte signal transduction pathway. The term includes antibodies made by conventional methods including polyclonals, monoclonals or fragments thereof, as well as genetically engineered or synthetic molecules, e.g., single chain antibodies, that contain a binding region that is the functional equivalent of an antibody in its binding specificity.

As used herein, "cytokine" includes those proteins which mediate much of the intercellular signalling required for an integrated response to a variety of external stimuli. Cytokines are potent mediators which interact with specific high affinity receptors on the cell surface. Cytokines have been shown to affect the function of all cell types involved in an immune response; to be involved in lymphopoiesis and haemopoiesis; and have been implicated in the pathophysiology of a large number of diseases. Lymphokines are the preferred cytokines in the claimed invention.

T lymphocytes can be stimulated with an antibody to a lymphocyte surface receptor in vitro, for short time periods. Optionally, one or more cytokines also can be present during stimulation. The time periods for stimulation can be less than about 24 hours, for as little as 30 minutes, and preferably for 12-18 hours. These cells have a high therapeutic efficacy upon in vivo injection. The anti-CD3-stimulated cells are less toxic than cells cultured in IL-2 for several days because the anti-CD3.stimulated cells cause less acute pulmonary toxicity. Similarly, because the anti-CD3 stimulated cells can multiply in number in the presence of IL-2, small numbers of injected anti-CD3 stimulated cells can proliferate to large numbers following in vivo exposure to IL-2. Thereby, fewer cells can be administered.

Alternatively, T lymphocytes can be stimulated in vitro with antibodies to more than one lymphocyte surface receptor. Optionally, one or more cytokines can be also present during stimulation. The stimulation of T lymphocytes in vivo can be accomplished with antibodies to one or more T lymphocyte surface receptors; with one or more cytokines; or with a combination of antibodies and cytokines.

The antibody to a T lymphocyte surface receptor can be made by well known and conventional methods, for example those described in *Current Protocols in Immunology*, Vol. I, J. E. Coligan, A. M. Jruisbeek, D. H. Margulies, E. M. Shevach and W. Strober (eds.), Green Publishing Associates and Wiley-Interscience, 2.4.1-2.10.3 (1991). Antibodies to a surface receptor that can be used alone, or in combination with other antibodies to different T cell surface receptors, in a method for the activation of T lymphocytes, include, but are not limited to, anti-CD2, anti-CD3, anti-CD4, anti-CD5, anti-CD6, anti-CD7, anti-CD8, anti-CD28, anti-CDw29, or anti-CD45R. It is preferably an anti-CD3 MAb. The anti-CD3 MAb can be, but is not limited to, OKT3, WT32, Leu-4, SPV-T3c, RIV9, 64.1, 145.2C1, etc. More preferably, the anti-CD3 MAb is the anti-murine CD3 MAb 145.2C11, which has been identified by O. Leo et. al., *Proc. Natl. Acad. Sci. USA*, 84, 1374 (1978), and is available from the American Type Culture Collection (ATCC). T lymphocytes treated with anti-CD3 MAb for less than about 24 hours are preferably treated with a total dose of about 10 ng/ml, or less, anti-CD3 MAb. Mouse anti-human OKT3 is available from the Ortho Division of Johnson and Johnson. Humanized versions of the antibodies will have utility for T cell activation in vivo during treatment.

The anti-CD3 stimulation induces the expression of the IL-2 receptor. Stimulated T cells are collected and placed in the body of an organism, preferably a mammal, such as a mouse or a human, where they develop immunotherapeutic activity, e.g. cytotoxic activity, or lymphokine production, upon administration of IL-2. More preferably the cells are placed in the body of a human for immunotherapeutic treatment. The cells can be administered to the patient using any of the conventional and well known methods and routes. S. A. Rosenberg, U.S. Pat. No. 4,690,915. These routes include intravenous, intraarterial or intracavitary administration, encompassing intrapleural, intraperitoneal, intrathecal, intravesicular, and the like. With the administration of an effective amount of IL-2 in vivo, the cells display an enhanced proliferation and antitumor activity. The administration of IL-2 preferably occurs over a period of about 7 days. The amount of IL-2 effective for enhancing cell proliferation and immunotherapeutic activity in vivo depends on the mammal being treated. For example, about 10,000-70,000 units/day of IL-2, preferably about 50,000 units/day of IL-2, are administered to mice, and about $1'10^6$ to $6 \times 10^6$ International Units/m$^2$/day are administered to humans.

It is preferred that the cells are initially stimulated for less than 24 hours with anti-CD3 MAb, with or without any IL-2 present. However, it is within the scope of the invention to include IL-2 with the anti-CD3 MAb in the initial culture, if desired. Although this is possible and produces similar results, it is not necessarily preferred, at least because of the expense of IL-2. Rather, it is more efficient to stimulate cells with anti-CD3 MAb alone, collect the stimulated cells, infuse the stimulated cells into an immunosuppressed mammal, and then administer IL-2 to the mammal.

Interleukin-2 is a commercially available T-cell growth factor. It can be naturally occurring IL-2, such as might be derived from cultured rat splenocytes or from the Jurkat cell line, or it can be recombinant IL-2 (rIL-2). It is believed that other cytokines can also be used in the present invention to produce the cytokine-activated cells. The naturally occurring cytokine, or recombinantly produced cytokine can be used. These include, but are not limited to, IL-1, IL-4, IL-6, IL-12, TNF, GM-CSF, interferon, etc. It is envisioned that they can be used alone, in sequence, or in combination with other cytokines, including IL-2, in the culturing medium or administered to the patient. Commercial sources of recombinant human and murine cytokines are available. *Current Protocols in Immunology*, Vol. I, J. E. Coligan, A. M. Kruisbeek, D. H. Margulies, E. M. Shevach and W. Strober (eds.), Green Publishing Associates and Wiley-Interscience, 2.4.1–2.10.3 (1991).

Although free cytokines such as IL-2 can be used in the method of the present invention, the cytokine is preferably incorporated into liposomes as a delivery system. These phospholipid vesicles can contain varying amounts of cytokine or other bioactive compounds, depending on the type of interaction between the solute and the phospholipid. Methods for the preparation of liposome-encapsulated cytokines are disclosed in co-pending U.S. application Ser. No. 07/382,778, the disclosure of which is incorporated in its entirety herein by reference.

Several routes of administration can be used for the administration of liposomes, for example, intravenous, subcutaneous, intraperitoneal, and oral delivery. An important advantage of liposomal delivery is the change in tissue distribution and binding properties as compared to the free forms of the bioactive ingredient, resulting in enhanced therapeutic index and decreased toxicity.

It has been discovered that there is a marked decrease in the therapeutic efficacy of adoptively transferred T lymphocytes from murine hosts bearing tumors for >30 days (late tumor-bearing mice or late TBM) as compared to normal mice and mice bearing tumor for <21 days (early tumor-bearing mice or early TBM).

In vitro analysis of the functions of the T lymphocytes from late TBM showed an apparently normal proliferative response to anti-CD3 and IL-2 and adequate lymphokine production from CD4+ cells. A significant decrease in the cytotoxic function of CD8 cells, however, was observed. The decreased cytotoxicity was not due to cell-mediated suppression. The expression of genes encoding for lytic molecules such as TNFα and granzyme B was significantly decreased.

T lymphocytes from late TBM lose the expression of the ζ and CD3 γ chains. The ζ chain is in turn replaced by the expression of the Fcγζ chain, a member of the ζ family of chains. These lymphocytes also exhibit a marked decrease in the Lck protein. These changes result in decreased ability to mobilize $Ca^{+2}$ and in an altered pattern of tyrosine phosphorylation.

Similarly, the expression of ζ protein in human cancer patients was undetectable or markedly reduced compared to healthy controls. The expression of ζ protein was analyzed by Western blot in human cancer patients. Equal numbers of cells isolated from the peripheral blood of two patients with renal cell carcinoma, one patient with liver metastases of an ocular melanoma and a healthy individual were analyzed using anti-ζ rabbit serum. Expression of ζ protein was detected in the healthy control. The expression of ζ was undetectable in the sample taken from one patient with renal carcinoma and the patient with liver metastases of an ocular melanoma. The expression of ζ protein was reduced by 95% in the second patient with renal cell carcinoma. The cancer in each of these patients was present for greater than 30 days.

Progression of cancer leads to immunosuppression of T lymphocytes. Loss in the antitumor effects of T cells in adoptive immunotherapy is correlated with a significant decrease in the cytotoxic function of CD8+ cells and changes in protein expression. The observed changes in protein expression in the immunosuppressed T cells include the complete loss, or marked decrease, in the expression of the TCR subunit proteins ζ and CD3+ the appearance of Fcεγ; and the decreased expression in the signal transduction pathway protein Lck. Functional correlates are the loss in the ability to mobilize $Ca^{+2}$ and an altered pattern of tyrosine phophorylation.

These observations have great utility in assays designed to determine the level of immunosuppression in a patient being evaluated for adoptive immunotherapy. Changes in the expression of selected proteins known to be predictive of the level of immunosuppression of T lymphocytes in a patient being evaluated for adoptive immunotherapy are assayed. Decreased expression of selected TCR subunit proteins such as ζ and CD3 γ; or decreased expression of selected T cell signal transduction pathway proteins such as Lck; or the expression of Fcεγ in T cells or T cell subsets, are diagnostic of the immunosuppressed state. These changes in protein expression in T lymphocytes or T cell subsets are correlated with loss in the ability to stimulate the T cells for effective adoptive immunotherapy.

The response in humans and other animals will correlate with that observed in the murine system. Complete or marked decrease in the expression of ζ protein was observed in three human cancer patients having tumor for 30 days. It is expected that decreased expression of TCR subunit proteins such as ζ and CD3 γ; the expression of Fcγε in the T lymphocytes; and the decreased expression in signal transduction pathway proteins such as Lck, will correlate with similar changes in T cell function including loss of cytotoxicity and loss in the ability to stimulate these. It is expected that NK cells, which also normally express ζ protein, will exhibit decreased immune responsiveness with loss in ζ expression.

In determining the patient's therapeutic plan, the physician will assay the expression of these proteins in order to evaluate the level of immunosuppression of the patient's own T lymphocytes and to determine the likelihood of success that these cells can be stimulated for effective autologous adoptive immunotherapy. It is further contemplated that T cells evaluated in this fashion can be used in allogeneic and syngeneic treatment protocols where a patient's own T cells are immunosuppressed. Even in instances in which adoptive immunotherapy is not contemplated, it is expected that evaluation of the level of immunosuppression will aid the physician in determining when to treat with antibacterial agents, immunostimulating drugs, etc.

Many different conventional and well known assay methods can be used to evaluate the level of expression of selected proteins in T lymphocytes. Samples of tissue or fluid are isolated from the patient and the level of expression of the selected TCR subunit protein, FCεγ, or selected protein in the T lymphocyte signal transduction pathway is determined. These samples are taken from tumor tissue, splenic or lymphatic tissue, peripheral blood cells, cerebrospinal fluid, pleural effusions, ascites, etc.

A protein extract of the sample can be analyzed directly to determine the level of expression of protein. Alternatively, T cells, or T cell subsets, are purified before determining the level of expression of the selected protein. T cells and T cell subsets can be purified by any of a variety of conventional techniques such as rosetting followed by Ficoll-Hypaque gradient centrifugation, indirect panning, antibody/complement-mediated cytotoxicity, immunomagnetic purification, flow cytometry, etc. Additionally, the TCR can be immunoprecipitated using an antibody such as anti-CD3 ε. The subunit proteins comprising the TCR are analyzed by Western blot.

The level of expression of the protein is determined using well known techniques such as immunofluorescence, ELISA, Western blot analysis, etc. An extract for analysis of protein by any of these well known techniques is made by conventional methods from the tissue or fluid sample, or T cells or T cell subsets prepared from these samples. An antibody which specifically detects the selected protein, and which is conjugated to a known label, is prepared by conventional methods.

Patients are selected for autologous adoptive immunotherapy whose level of expression of said protein is at or above the threshold for response to lymphocyte stimulation. The threshold level for response to lymphocyte stimulation must be empirically derived for each combination of disease and selected protein. For example, with one combination of selected protein and disease, it may be found that the selected protein must be produced at levels substantially equivalent to that found in healthy individuals in order for autologous adoptive immunotherapy to be effective. With yet another combination of selected protein and disease, autologous adoptive immunotherapy may still be effective with only a low level of expression of the selected protein.

Alternatively, the expression of the gene encoding the selected protein in T cells or T cell subsets is ascertained by any of a variety of methods including Northern hybridization or in situ hybridization. RNA is isolated from the tissue or cell samples if the gene is known to only be expressed in T lymphocytes, or alternatively, from purified T cells or T cell subsets prepared from these samples, using conventional methods. The RNA is hybridized with labeled DNA or hybridization probe which specifically detects the mRNA encoding the selected protein.

Alternatively, patients are selected for adoptive immunotherapy on the basis of their expression ratio. The expression ratio (E.R.) is the number of T cells which express a selected TCR subunit protein, or protein in the T lymphocyte signal transduction pathway, divided by the total number of T cells counted. For example, the expression ratio can be determined by means of two-color or three-color flow cytometry. *Current Protocols in Immunology*, Vol. I, J. E. Coligan, A. M. Jruisbeek, D. H. Margulies, E. M. Shevach and W. Srober (eds.), Green Publishing Associates and Wiley-Interscience, 5.1.1–5.4.15 (1991). For components of the TCR that are on the interior of the membrane or components of the signal transduction pathway, the cell can be made permeable to the label. For example, lymphocytes isolated from the patient are exposed to two different antibodies each of which is conjugated to a different dye. One antibody is used to detect cells expressing the selected TCR subunit protein, or protein in the T lymphocyte signal transduction pathway, and this antibody is conjugated to a dye such as fluorescein isothiocyanate (FITC). The second antibody binds to a protein found in all T cells, such as CD3, and this antibody is conjugated to a second dye such as phycoerythrin. The fraction of T cells expressing the selected TCR subunit protein or T lymphocyte signal transduction pathway protein is determined by analysis of the samples using flow cytometry.

Patients are selected for autologous adoptive immunotherapy whose level of expression of said protein is at or above the threshold level for response to lymphocyte stimulation. The threshold level for response to lymphocyte stimulation must be empirically derived for each combination of disease and selected protein. For example, with one combination of selected protein and disease, it may be found that at least 50% of the T cells must express the selected protein (E. R.=0.5) if autologous adoptive immunotherapy is to be effective. With yet another combination of selected protein and disease, expression of the protein in at least 70% of the T cells (E. R.=0.7) may be required if autologous adoptive immunotherapy is to be effective.

It is expected that the methods of the present invention can be used in the treatment of a great variety of diseases characterized by the malfunctioning of the immune system. Such diseases include those that result in progressive immunosuppression as well as diseases in which self is recognized as foreign and therefore, an autoimmune response is established.

Diseases which result in progressive immunosuppression include cancers of any tissue including leukemia, Hodgkin's disease, lung cancer, colon cancer, gliomas, renal cell carcinoma, etc. Progressive immunosuppression is observed in a great variety of infections including those that are intracellular such as leprosy, tuberculosis, leishmania, etc.; those that are extracellular such as sepsis, etc; diseases of viral etiology such as those caused by HIV, cytomegalovirus, Epstein Barr, etc.; parasitic infections such as schistosomiasis, malaria, etc. It is contemplated that in determining the patient's therapeutic plan, the physician will assay the expression of selected TCR subunit proteins, the expression of FCεγ, or the expression of selected proteins in the T cell signal transduction pathway, in order to evaluate the level of immunosuppression of the patient's own T lymphocytes and to determine the likelihood of success that these cells can be stimulated for effective autologous adoptive immunotherapy.

Diseases which result in the establishment of an autoimmune response include lupus, autoimmune thyroiditis, scleroderma, rheumatoid diseases such as rheumatoid arthritis, etc. It is contemplated that in evaluating the efficacy of the patient's therapeutic plan, the physician will assay the expression of selected TCR subunit proteins, the expression of FCεγ, or the expression of selected proteins in the T cell signal transduction pathway, in order to evaluate the level of immunosuppression of the patient's own T lymphocytes. Such information will be useful in evaluating the efficacy of patient treatment with immunosuppressive drugs, etc.

It is expected that conventional treatments and protocols can be used to complement and supplement the methods of the present invention. It was found that tumor cell supernatant suppressed the in vitro cytolytic activity of normal lymphocytes. Therefore, it is expected that conventional treatments can be used to complement and supplement adoptive immunotherapy. As the tumor size or load of the patient is decreased using non-biological treatments, the level of immunosuppression will also abate. Additionally, agents are known which appear to reverse immunosuppression. These treatments or agents can be followed or supplemented with autologous adoptive immunotherapy. Effective timing of autologous adoptive immunotherapy can be predicted by measuring the level of immunosuppression in the patient by determining the level of expression of selected TCR subunit proteins; Fc$\epsilon\gamma$ in T lymphocytes; and proteins in the T lymphocyte signal transduction pathway. The methods that can be used to supplement or complement autologous adoptive immunotherapy include surgery; radiation or treatment with chemotherapeutic or pharmacological agents. The chemotherapeutic or pharmacological agents include all cytokines; agents which reduce tumor size or load including cyclophosphamide, adriamycin, steroids, etc.; growth hormones; cimetidine; chloroquine; non-steroidal anti-inflammatories such as aspirin, ibuprofen, indomethacin, etc.; levamisole; etc.

It is expected that several different strategies are available to circumvent immunosuppression of T lymphocytes. It is expected that immunotherapeutic activity of T lymphocytes can be restored by recombinant methods. The level of expression of selected TCR subunit proteins or T lymphocyte signal transduction pathway proteins can be restored in immunosuppressed cells by introducing into said cells an expression vector comprising the gene encoding the selected protein. The expression of the gene in the recombinantly engineered cells restores normal levels of the protein to the lymphocytes. These recombinantly engineered lymphocytes can then be stimulated for adoptive immunotherapy using any of the alternative methods herein described.

Well known and conventional methods can be used for the construction of the expression vector carrying the selected gene of interest as well as for the introduction of said vector into immunosuppressed T cells. The gene is operably linked to a promoter, which can be a regulatable promoter. The vector can be introduced into T lymphocytes using well known transfection protocols such as calcium phosphate transfection or transfection by electroporation. The selected gene can be introduced and expressed in T cells using well known retroviral vectors. Current Protocols in Molecular Biology, F. M. Ausubel et. al. (eds.), Greene Publishing Associates and Wiley-Interscience, 9.0.1–9.14.3 (1989).

It is expected that the immunorestorative agents identified using the methods of the claimed invention will have utility in the treatment of diseases characterized by progressive immunosuppression by reversing immunosuppression. These agents are identified by providing a mammaliam T lymphocyte preparation wherein the level of expression of at least one selected TCR subunit protein or protein in the signal transduction pathway is subnormal compared to healthy individuals of the same mammalian species; the lymphocyte preparation is cultured in the presence of an agent suspected of reversing immunosuppression; and the level of expression of the selected protein is determined. Alternatively, the agent is administered to a subject with subnormal expression of a TCR subunit protein or protein in the T lymphocyte signal transduction pathway and the level of expression of said protein is determined.

Agents capable of significantly increasing the level expression of selected TCR subunit proteins or proteins in the T lymphocyte signal transduction pathway can be used in a method of reversing immunosuppression in a diseased animal or human. The agent will be administered to the subject, optionally with or without T cell surface receptor antibodies and/or cytokines for the stimulation of lymphocytes, in order to reverse immunosuppression in the diseased subject. Alternatively, lymphocytes isolated from the subject will be treated in vitro with the agent and administered to the patient for adoptive immunotherapy. These lymphocytes can optionally be stimulated in vitro or in vivo,. with or without T cell surface receptor antibodies and/or cytokines.

It is expected that immunosuppressive agents identified using the methods of the claimed invention will have utility in the treatment of autoimmune diseases. These agents are isolated by providing a mammalian T lymphocyte preparation wherein the level of expression of at least one selected TCR subunit protein or protein in the signal transduction pathway is normal compared to healthy individuals of the same mammalian species; the lymphocyte preparation is cultured in the presence of an agent suspected of causing immunosuppression; and the level of expression of said protein is determined. Of particular interest in this regard are the soluble agents produced by tumor which cause T cell immunosuppression. Alternatively, the agent is administered to a healthy subject and the level of expression of at least one selected TCR subunit protein or protein in the lymphocyte signal transduction pathway is determined.

Agents capable of decreasing the level of expression of selected TCR subunit proteins or proteins in the T lymphocyte signal transduction pathway can be used in a method of inducing immunosuppression in an animal or human. The agents will be administered to the subject. Alternatively, lymphocytes isolated from the subject will be treated in vitro and then administered to the subject.

It is expected that the methods of the present invention will be useful in monitoring and facilitating transplantation of organs and tissues. A patient is currently prepared for a transplant by means of various treatments designed to increase the level of tolerance. These treatments include repeated transfusions with white blood cells. It will be possible to monitor the level of expression of selected TCR subunit proteins, FC$\epsilon\gamma$, and proteins in the T lymphocyte signal transduction pathway during preparation of the patient in order to determine the level of immunosuppression in the patient and thereby ascertain when patients are sufficiently immunosuppressed to receive the transplant.

It is expected that the methods of the present invention can be used to determine the level of immunosuppression in the patient and thereby provide information needed to properly time treatment to maintain tolerance. Agents isolated using the screening methods of the present invention, capable of increasing immunosuppression in the patient, are expected to have utility for the successful preparation and maintenance of the transplant patient.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLE 1

Loss of Antitumor Effects of T Cells Isolated from Long-term Tumor-Bearing Mice T cells isolated from late TBM have no antitumor effects when used in adoptive immunotherapy. The generation of T-activated killer (T-AK) cells was accomplished as described in C. M. Loeffler et. al., *Cancer Res.* 51, 2127 (1991), which is incorporated herein by reference. C57BL/6 murine splenocytes were placed on a Ficoll-Paque gradient (Pharmacia) for isolation of lymphocytes. After washing with HBSS (GIBCO, Grand Island, NY) two times, red blood cells (RBC) were lysed with distilled water and the remaining mononuclear cells counted. The cells were then placed over a mouse T cell rapid affinity chromatography column (Biotex Laboratories Inc., Edmonton Canada) for T-cell enrichment. Cells were washed with HBSS two times, activated with anti-CD3 MAb (145-2C11) and IL-2 (specific activity, $1.5 \times 10^7$ U/mg; Hoffmann-LaRoche Inc., Nutley, NJ). T-enriched cells were incubated in culture flasks at a concentration of $1.5 \times 10^6$ cells/ml of TCM consisting of Rosewell Park Memorial Institute (RPMI) 1640 (available from GIBCO, Grand Island, NY) supplemented with 25 mM HEPES [N-2-hydroxyethyl)piperazine-N'-(2-ethanesulfonicacid)],2 mM L-glutamine, 5% fetal calf serum, 100 U/ml penicillin, 100 μg/ml streptomycin, 10 mM non-essential amino acids, 100 mM sodium pyruvate, and 25 μM 2.mercaptoethanol. To generate T-AK cells, 2 μg of 145-2C11 MAb was added per ml of TCM. Cells were incubated overnight at 37° C. in 5% $CO_2$ after which they were harvested, washed twice in HBSS, resuspended in HBSS containing 30 U/ml of IL-2, counted and injected into mice.

Methods for demonstrating the therapeutic efficacy of T-AK cells used in conjunction with liposome-encapsulated IL-2 (IL-2 liposomes), were done as described in C. M. Loeffler et. al., *Cancer Res.* 51, 2127 (1991), which is incorporated herein by reference. Approximately $3.0 \times 10^5$ MCA-38 cells in 0.5 ml of HBSS were injected intrasplenically in 6- to 8-week old C57BL/6 mice using a 30 gauge needle. Each experimental group consisted of at least 10 C57BL/6 mice. After three days, mice received a single intravenous injection of $4.0 \times 10^7$ T-AK cells from either normal mice, early TBM (subcutaneous tumor present for 14-21 days) or late TBM (subcutaneous tumor present for greater than 30 days). In addition, mice received once-daily intraperitoneal injections of IL-2 liposomes (50,00 U per day) on days 3-7 following tumor inoculation. The number of hepatic metastases was evaluated in each therapeutic group on day 12 after tumor inoculation. One to 2 ml of a 15% India ink solution was injected into the superior mesenteric vein of anesthetized mice. The liver was removed and placed in Fekete's solution (30 ml formalin and 15 ml glacial acetic acid in 300 ml of 70% ethanol). Hepatic metastases were counted and a Student's unpaired T-test was used to evaluate the significance of differences between treatment groups.

The data presented in FIG. 1 illustrates representative results obtained in three separate experiments. Untreated mice had $236 \pm 30$ liver metastases by day 11. Mice treated with T-AK cells from a non-tumor-bearing mouse (normal) had $99 \pm 23$ metastases while T-AK cells from early TBM produced an even greater reduction in the number of metastases to $48 \pm 16$. T-AK cells obtained from late TBM failed to produce any therapeutic effect because hepatic metastases numbered $229 \pm 41$. The therapeutic efficacy of T-AK cells is therefore dramatically reduced when these cells are obtained from late TBM.

EXAMPLE 2

Significant Decrease in In Vitro Cytotoxicity in T Lymphocytes from Late TBM.

The in vitro cytotoxicity of lymphocytes from late TBM is significantly decreased. Standard chromium release assays were performed using as effectors, T-AK cells which were maintained in culture with 100 U of rIL-2 after the initial stimulation with anti-CD3. Assays were performed on days 2, 4, and 7 of culture. Tumor targets ($4 \times 19^6$/ml) were incubated with 150 μCi Na$_{51}$-CrO$_4$ (1000 μCi/ml; New England Nuclear Products, Boston, MA) at 37° C. for 60 min. The targets were washed twice with TCM, resuspended in media, and counted. T-AK effector cells were washed twice and then aliquoted in triplicate in U-bottom microtiter plates (Costar) and serially diluted 2.fold to yield effector:target cell ratios ranging from 24:1 to 3:1. Five thousand targets were added per well. Spontaneous release wells contained target cells in culture media only. The maximum release well contained target cells in detergent. Plates were incubated for 4 h at 37° C. in 5% $CO_2$. The supernatant was harvested and radioactivity was counted in a gamma counter (LKB 1272). The percentage of specific cytotoxicity was determined by the formula:

$$\frac{\text{Experimental mean cpm} - \text{spontaneous mean cpm}}{\text{Maximal mean cpm} - \text{spontaneous mean cpm}} \times 100 = \% \text{ of cytotoxicity}$$

Figure 3:
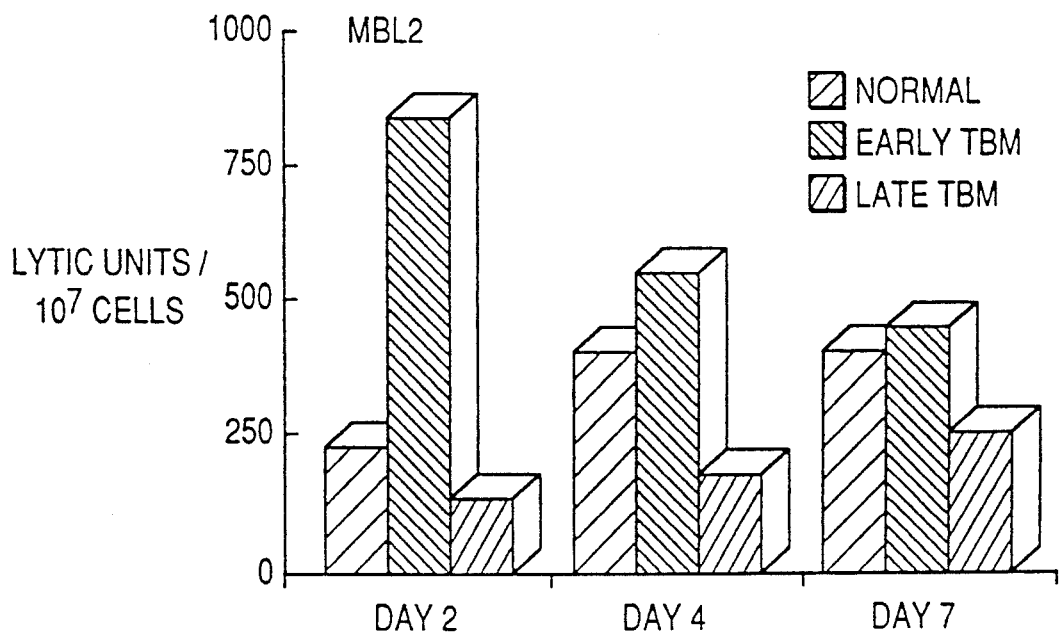
FIG. 3 illustrates the cytolytic activity of normal, early and late TBM T-AK cells against MBL2. Enriched T cells were activated with anti-CD3 and cultured in TCM containing 100 U rIL-2/ml. Lytic activity was tested on days 2, 4 and 7 of culture in a 4-h chromium release assay.
Figure 2A:
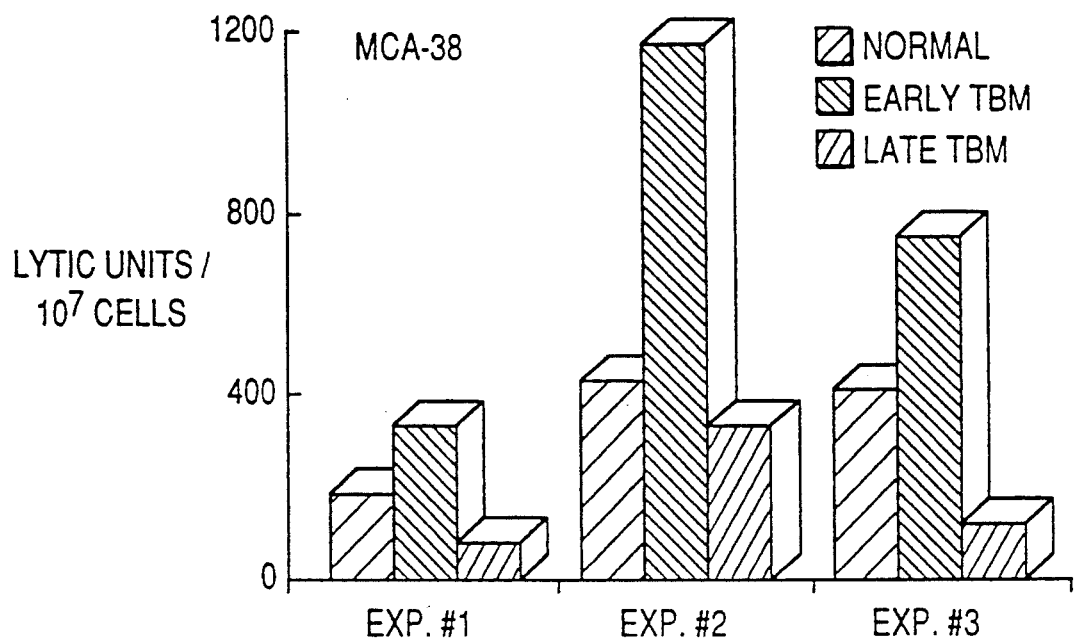
FIGS. 2A, 2B and 2C illustrates the cytolytic activity of normal, early and late TBM T-AK cells against MCA-38 (2A colon carcinoma), MBL2 (2B lymphoma) and RENCA (2C renal cell carcinoma) tumor cell lines. Enriched T cells were activated with anti-CD3 and cultured in tissue culture medium (TCM) containing 100 U recombinant interleukin—2m/ (rIL-2/ml). Lytic function was tested on day 2 of culture.
Figure 2B:
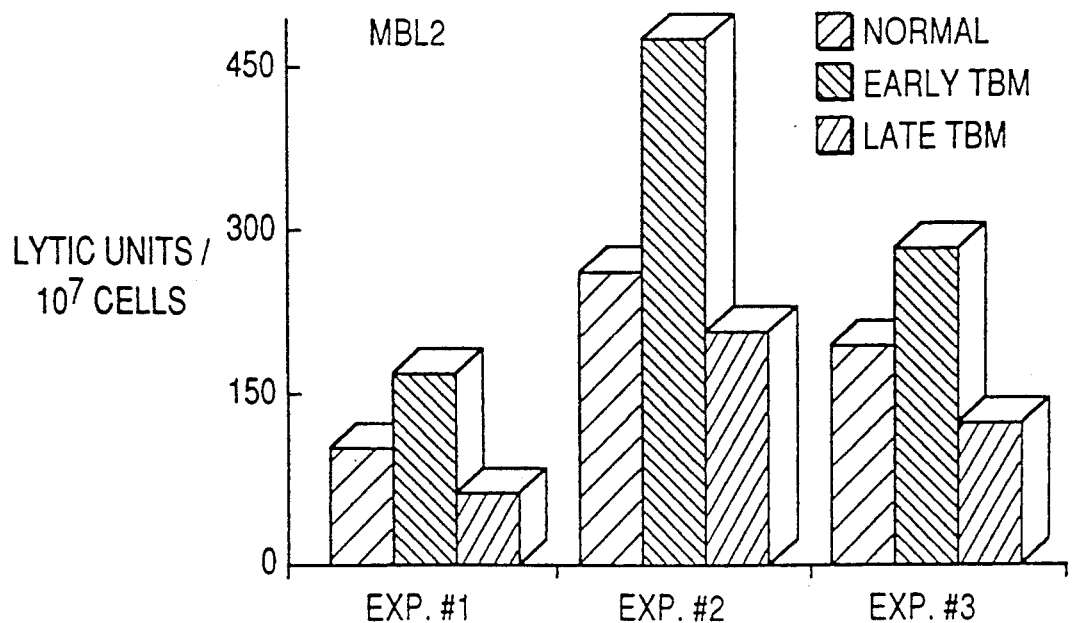
Figure 2C:
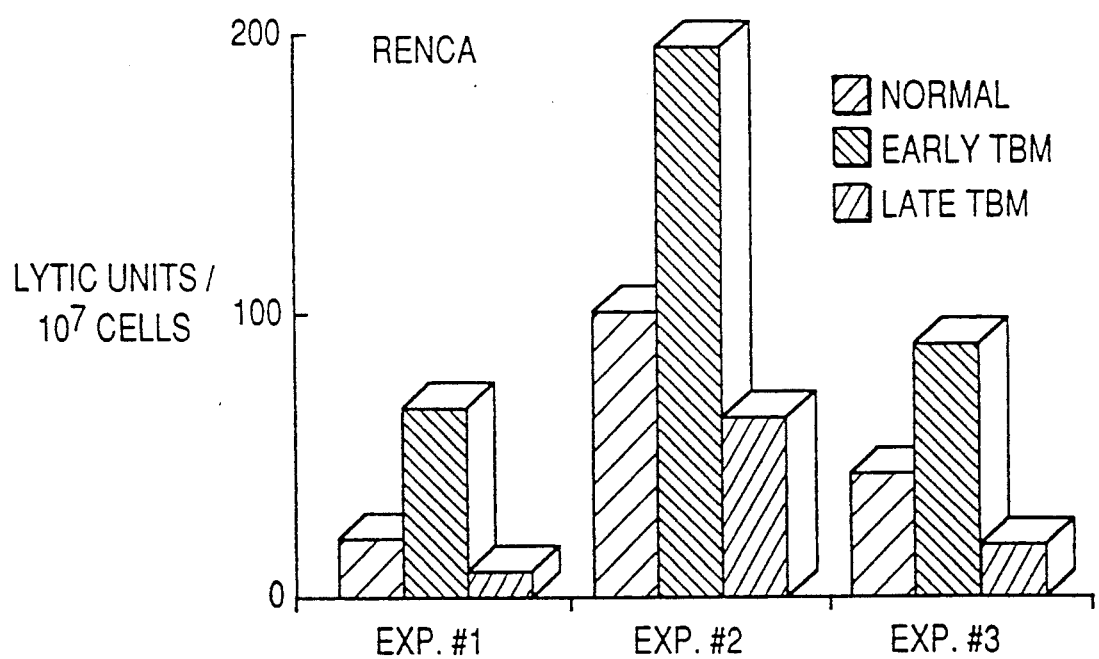

At day 2 of culture, cytolytic activity was consistently highest in the early TBM cells (FIG. 2) while that of both non-tumor-bearing (normal) or late TBM cells was lower. Lytic function of cells from normal mice on day four of culture had increased significantly, but it was still highest in early TBM (FIG. 3). Late TBM lymphocytes had the lowest lytic function.

Only after 7 days in culture did lymphocytes from late TBM show any significant increase in lytic function (FIG. 3). Lytic activity was also observed against the syngeneic target MBL2 (lymphoma) and an allogeneic target, RENCA (renal cell carcinoma). The absolute levels of cytotoxicity varied with the targets, but early TBM cells were consistently the most lytic, and the late TBM cells always had the lowest activity.

Cytotoxicity assays were performed using CD8+-enriched preparations from early and late TBM. Enriched T-cell preparations were made by passing a single cell splenocyte suspension through a T-cell column (Biotex Laboratory Inc., Edmonton, Canada) following the kit instructions. To enrich for CD8+ cells, T-enriched cells were incubated with 1 μg/$1.0 \times 10^6$ cells of anti-L3T4 (500 μg/ml; Becton Dickinson, Mountain View, CA) for 30 min at 4° C. The cells were washed twice in HBSS. Goat anti-mouse IgG Fc-specific coated magnetic beads (Advanced magnetics Inc., Cabmridge, MA) were washed with PBS twice and incubated with PBS and mixed with the T-enriched cells at a bead:cell ratio of 25:1 at 4° C. for 30 min and then separated on a magnetic separator (Advanced Magnetics). The last step was repeated twice. Unbound cells were removed and washed twice with HBSS. CD8+-enriched cells had less than 2% CD4+ contaminating cells. Phenotypic analysis of the enriched cell preparations showed greater than 95% CD8+.

CD8+ enriched cells showed lytic activity similar to that of unseparated lymphocytes (Table 1). To eliminate the potential confounding effects of even small numbers of contaminating cells, CD8+ cells were also positively sorted by FACS, cultured with anti-CD3+IL-2 and tested for lytic function. Positive cell selection by FACS was performed with T-enriched cells from fresh splenocyte preparations (greater than 95% Thy 1.2+ cells). These cells were incubated with 1 $\mu$g/$1.0 \times 10^6$ cells of anti-Lyt.2 FITC and anti-L3T4 (500 $\mu$g/ml; Becton Dickinson) for 30 min at 4° C. The cells were then sorted into FITC+ (CD8+ cells) and PE+ (CD4+ cells) on a FACStar Plus flow cytometer (Becton Dickinson).

The lytic activity of the early TBM CD8+ lymphocytes was again the highest while that of late TBM cells was the lowest (Table I). In all experiments, the results remained similar regardless of whether the effector cells were enriched T cells, enriched CD8+ or pure CD8+ cells. The increase in cytotoxicity seen in late TBM CD8+ cells after seven days in culture may be due to an increase in the lytic function of the originally suppressed CD8+ cells or due to the expansion of a small subset of CD8+ cells which were never suppressed.

TABLE I

Cytotoxic activity of T cells from normal mice, early TBM, and late TBM[a]

| | Lytic U/$10^7$ cells |
|---|---|
| T enriched cells | |
| Normals | 259 |
| Early TBM | 319 |
| Late TBM | 189 |
| CD8+ cells (CD4+ depleted) | |
| Normals | 254 |
| Early TBM | 469 |
| Late TBM | 162 |
| CD8+ cells (positive sort) | |
| Normals | 278 |
| Early TBM | 1161 |
| Late TBM | 125 |

[a]Cytolytic activity of T-enriched, CD8+ cells obtained by CD4+ depletion or cell storing. Cells were activated with anti-CD3 and cultured in TCM with 100 U IL-2/ml for 3 days.

EXAMPLE 3

Pehnotypic Analysis of T-Enriched Cell Preparations from Fresh Splenocytes of Normal Mice, Early TBM and Late TBM The abnormal activity of late TBM cells is not related to large alternations in T-cell subsets or distributions. To determine if a difference in the percentage of T-lymphocyte subsets could explain the difference in lytic function, phenotyping was done. Fresh splenocytes from the various groups of mice were enriched for T cells and purified to remove contaminating tumor cells. The data was obtained from cell preparations that were greater than or equal to 95% Thy 1.2+.

There was a consistent, but not significant decrease in the L3T4+ populations from late TBM (Table II). The CD4/CD8 ratios in these mice, however, remained within normal limits. The phenotypes of fresh splenocytes not enriched for T cells, obtained from the same groups of mice, did not show any significant change in the cell subsets. Large alternations in T-cell subsets or distribution, therefore, is not related to the abnormal activity of late TBM.

TABLE II

Phenotypic analysis of T-enriched cells from normal mice, early TBM, and late TBM[a]

| | Thy 1.2 | CD 3 | Lyt.2 | L3T4 | Mac 1 |
|---|---|---|---|---|---|
| Normals | 98% | 86% | 37% | 54% | 2% |
| Early TBM | 97% | 89% | 30% | 58% | 3% |
| Late TBM | 95% | 86% | 34% | 48% | 3% |

[a]Phenotypic analysis of T-enriched cells from normal and tumor-bearing mice (TBM). Flow cytometry was performed on T lymphocytes isolated from spleens of mice bearing tumor for different lengths of time. T lymphocytes were enriched on a T-cell column (Cellect, Biotex) immediately after isolation.

EXAMPLE 4

No Major Differences Observed in the Levels of Lymphokines in Supernatants of Activates T-Enriched Cells from Normal Mice, Early TBM and Late TBM In order to determine if inadequate function of the CD4+ helper cell subset was the principal cause of the decreased immunological responsiveness in late TBM, lymphokine levels in the supernatants of activated T-enriched cells from normal mice, early TBM and late TBM were compared. Samples of supernatants were collected at 24, 48 and 72 h. IL-1$\alpha$ was measured using mouse Interest I-$\alpha$ Elisa (Genzyme, Cambridge, MA). Biologically active protein was confirmed using the IL-1 mouse thymocyte bioassay. IL-2 levels were tested with the IL-2 Elisa Kit (Collaborative Research, Inc., Bedford, MA) and confirmed with the IL-2 bioassay using the IL-2.dependent cell line, CTLL.2 (ATCC). IL-6 levels were measured with the murine IL-6 Elisa Kit (Endogen Inc., Boston, MA) and confirmed with the murine bioassay utilizing the plasmacytoma cell line T1165 (Genetics Institute). Total murine interferons were measured with the L929 (ATCC) virus bioassay. TNF-$\alpha$ levels were measured with the 1929 mouse fibroblast cell line (ATCC).

There were no major differences in the levels of lymphokines measured in the early and late TBM T-AK cultures in three different experiments. The data after 48 h in culture, from two of these experiments, is shown in Table III. Significant differences in lytic function were observed in these same experiments. Lymphokine production was therefore quantitatively and qualitatively similar in the supernatants of activated T-enriched cells from normal mice, early and late TBM.

TABLE III

Lymphokine levels in supernatants of activated T-enriched cells from normal mice, early TBM and late TBM[a]

| | IL-1[b] | IL-2[c] | IL-6[b] | IFN[c] |
|---|---|---|---|---|
| Experiment #1 | | | | |
| Normal | 24 | 3.0 | 850 | 20 |
| Early TBM | 48 | 6.5 | 1000 | 60 |
| Late TBM | 40 | 6.0 | 1250 | 40 |
| Experiment #2 | | | | |
| Normal | 0 | 4.5 | 1200 | 16 |
| Early TBM | 90 | 7.5 | 1250 | 130 |
| Late TBM | 75 | 9.0 | 1250 | 180 |

[a]Lymphokine levels in supernatants of T-enriched cells from normal and TBM activated with anti-CD3. Samples were obtained at 24, 48, and 72 h. Data presented are from 48 h.
[b]pg/ml
[c]I.U./ml

EXAMPLE 5

CD4+ Cells from Late TBM Have Adequate Helper Function.

CD4+ lymphocytes in late TBM are more active as helper cells than CD4+ cells from normal animals. Mixing experiments were done to test whether CD4+ cells from late TBM would enhance or suppress the development of lytic function in normal CD8+ cells. Purified CD4+ and CD8+ lymphocytes were cocultures in 24 mm wells separated by a membrane with 4 μm size pores. This pore size allows for free exchange of soluble components. Cytotoxicity assays were performed on day 2 of culture.

CD8+ cells from normal mice showed an increased lytic activity (655 L.U.) when cocultured with CD4+ cell from late TBM compared to their lytic activity (204 L.U.) in the presence of normal CD4+ cells (Table IV). CD4+ cells from late TBM were able to support the high lytic function of early TBM CD8+ lymphocytes (1075 L.U.) even better than normal CD4+ cells (482 L.U.). CD4+ lymphocytes are not responsible for suppressing the function of CD8+ cells in late TBM because these cells are more active as helper cells than CD4[30] cells from normal animals.

TABLE IV

CD4+ cells from late TBM do not suppress lytic function in CD8+ cells[a]

| Source of Cells | | | |
|---|---|---|---|
| Late TBM | Early TBM | Normal | Lytic U/$10^7$ cells |
| CD4+/CD8+ | — | — | 139 |
| — | CD4+/CD8+ | — | 1375 |
| — | — | CD4+/CD8+ | 204 |
| — | CD4+ | CD8+ | 1058 |
| CD8+ | CD4+ | — | 354 |
| CD4+ | — | CD8+ | 655 |
| CD4+ | CD8+ | — | 1075 |
| CD8+ | — | CD4+ | 104 |
| — | CD8+ | CD4+ | 482 |

[a]Mixing experiments were performed by combining freshly isolated cells subsets in 24 mm wells after stimulation with anti-CD3 and IL-2. Experiments were also performed utilizing Costar "Transwell" plates where the subsets are separated by a membrane containing 0.4 μm pore size. Lytic function was tested against MBL2 lymphoma three days after starting the culture.

EXAMPLE 6

CD8+ Cells from the Late TBM Do Not suppress other CD8+ Cells

CD8+ cells from late TBM are defective. CD8+ cells from ate TBM are poor in lytic activity when cocultured with CD4+ cells from any source. When cocultured with the most highly active CD4+ cells from early TBM, CD8+ cells from late TBM had ⅓ to ¼ the total lytic activity of CD8+ cells from normal mice or early TBM. Coculture experiments performed in regular 24 mm wells which permit cell-cell contact between CD4+ and CD8[3]+ cells showed very similar results where once again, CD8+ activity of CD8+ cells from normal mice or early TBM. mixing experiments using CD8+ cells from early and late TBM gave no indication that CD8+ cytolytic activity is suppressed by other CD8+ suppressor cells. Even in the presence of adequate helper function CD8+ cells from late TBM were weakly cytotoxic suggesting that CD8+ cells are the target of tumor-mediated immune suppression.

EXAMPLE 7

Inhibition of Cytotoxic Activity of Normal Cells by Supernatants from MCA-38 Cell Cultures The absence of suppressor activity within the lymphocyte subsets from late TBM suggested that the inhibiting signal(s) might originate from the tumor itself. Titration experiments were performed using increasing concentrations of supernatants from MCA.38 cell cultures making sure the concentration of IL-2 was kept constant. Lymphocytes were activated with anti-CD3 and cultured with 100 U/ml of IL-2. Cultures were started at $1.5 \times 10^6$ cells/ml and cell counts and cytotoxicity assays were performed on day 3 of culture.

The cytolytic activity of lymphocytes cultured in media containing as little as 30% supernatant from MCA.38 cells was decreased by 30–45% (Table V). TGF-$\beta$ is a tumor-associated cytokine that has been implicated in tumor-mediated immune suppression. Antibodies to TGF-$\beta$, however, did not diminish the inhibitory effects of the tumor supernatant. Two bioassays failed to detect any TGF-$\beta$ activity in the tumor supernatant.

Similar inhibitory effects were mediated by supernatants of the MBL-2 lymphoma The inhibitory effects of the tumor is therefore not limited to the MCA-38 model system. These data suggest that a soluble tumor product(s) inhibits the development of cytotoxic function in CD8+ cells in late TBM.

TABLE V

Suppression of in vitro cytolytic activity of normal lymphocytes by tumor cell supernatant[a]

| | Lytic U/$10^7$ cells | | |
|---|---|---|---|
| | Exp. 1 | Exp. 2 | Exp. 3 |
| Normals | 138 | 93 | 118 |
| 10% supernatant | 126 | 116 | 126 |
| 30% supernatant | 99 | 89 | 66 |
| 50% supernatant | 83 | 48 | 21 |

[a]Suppression of cytolytic activity of normal lymphocytes by supernatant of MCA-38 cells in culture. Lymphocytes were activated with anti-CD3 and cultured with 100 U/ml of IL-2. Various concentrations of supernatant from MCA-38 tumor cultures were titrated into the cell cultures. Cultures were started at $1.5 \times 10^6$ cells/ml and cell counts and cytotoxicity assays were performed on day 3 of culture.

EXAMPLE 8

Expression of RNA Encoding for cytolytic Proteins Granzyme B and TNF-α are Decreased in CD8+ Cells from Late TBM Whole cellular RNA from enriched T lymphocytes from normal mice, and early and late TBM were analyzed at different time points during culture by Northern hybridization in order to assess whether the decreased lytic function of T-AK from late TBM was related to the production of cytolytic effector molecules. Additionally, the CD4+ and CD8+ subsets obtained by depletion were also analyzed. The expression of RNA encoding TNF-α, granzyme B, IL-2, IL-2R, IFN-γ and IL-6 was determined. An 18s RNA was used to determine the relative quantities of RNA loaded onto the gels. To compensate for differences in loading, densitometric ratios between the expression of 18S and granzyme B of TNF-α were done.

The expression levels of IL-2, IL-2R, IFN-γ and IL-6 RNA were identical in the early and late TBM lymphocytes. The level of granzyme B mRNA, however, was 10-fold higher in the CD8+ cells from early TBM at 36 h of culture than in CD8+ from late TBM. The level of granzyme B mRNA in CD8+ cells from late TBM was also significantly lower than in normal CD8+ cells at 36 h as measured by densitometry. The expression of mRNA encoding granzyme B in the CD8+ cells from late TBM increased to levels comparable to that seen in early TBM at 36 h of culture only by day 8 of culture. It is not known whether the cells expressing granzyme B on day 8 in the late TBM cells were a small subset of cells which proliferated to detectable levels by day 8 or whether time in culture allowed the CD8+ cells to recover and regain cytolytic function.

The expression of TNF-α mRNA was also highest in the T lymphocytes of early TBM, measured at 36 h of culture, compared to that of normal mice or late TBM. The expression of TNF-α mRNA in T lymphocytes from late TBM increased to levels comparable to that seen in early TBM at 36 h of culture only by day 8 of culture.

EXAMPLE 9

Marked Changes in the Expression of $\zeta$ and CD3 $\gamma$ in T Lymphocytes from Late TBM Surface expression of the TCR-CD3 complex of T lymphocytes from normal and late TBM was analyzed. T lymphocytes from normal mice expressed the $\alpha\beta$ Ti complex; the $\delta$, $\epsilon$ and $\gamma$ chains of the CD3; as well as the $\zeta$ homodimer. T lymphocytes from late TBM, however, do not express the $\zeta$ or CD3 $\gamma$ chains.

Expression of the TCR-CD3 complex was measured by fluorescence intensity of the T cells after labelling with control fluorescein labeled IgG2A, anti-mouse $\alpha\beta$ (Pharmingen) or anti-CD3 (145-2C11). Phenotypic analysis demonstrated that the purified T cells from late TBM were CD3+ (97%), Thy 1.2+ (98%), $\alpha\beta$+ (98%), NK1.1- (<1%) with a normal CD4 (L3T4)/CD8 (Lyte2+) ratio. A comparison of the TCR-CD3 complex of T cells from normal mice and late TBM revealed no apparent changes in the expression of the TCR-CD3 complex as suggested by the fluorescent intensity. The antibodies used for phenotyping the TCR, however, only bind to one each of the seven chains in the TCR CD3 complex.

Further evaluation of the TCR-CD3 complex was done by surface labeling with u:Iodine, immunoprecipitation with anti-CD3 (145-2C11) and resolution by 2-D non-reducing-reducing SDS-PAGE. Approximately $5 \times 10^7$ T lymphocytes from normal mice and late TBM were labeled with [125]Iodine by the lactoperoxidase-glucose oxidase method. *Current Protocols in Immunology*, Vol. I, J. E. Coligan, A. M. Jruisbeek, D. H. Margulies, E. M. Shevach and W. Strober (eds.), Green Publishing Associates and wiley-Interscience, 8.11.1-8.11.4 (1991). After labeling, the TCR complexes were recipitated with 145-2C11 MAb, absorbed to protein G-sepharose and resolved by 2D non-reducing-reducing 14% SDS PAGE. Major changes in the TCR-CD3 components from T cells from late TBM were apparent. The $\zeta$ subunit protein was absent and there was a marked decrease in CD3$\gamma$. Additionally, a faint spot below the diagonal corresponding to a small protein was present which suggested that an Fc$\epsilon\gamma$ chain was associated with the TCR-CD3 complex. E. Reinherz, *J. Exp. M,ed.*, 175, 203 (1992).

Western blots using anti-$\zeta$ or anti-Fc$\epsilon\gamma$ confirmed these observations. Approximately $2 \times 10^7$ T cells from normal and late TBM were solubilized in lysis buffer (25 mM Tris pH7.4, 150 mM NaCl, 0.5% Triton-X 100, mM sodium orthovanadate, 10μg/ml aproptinin, 10 μg/m; leupeptin and 5 mM EDTA). The lysate was centrifuged and the supernatant was immunoprecipitated with rabbit anti-$\zeta$ antiserum, control normal rabbit serum, anti-CD3$\epsilon$ (145-2C11 MAb) or control anti-human CD4 (OKT4). Immunoprecipitate was resolved by SDS-PAGE and blotted with anti-$\zeta$ rabbit serum. T lymphocytes from late TBM lost the expression of the $\zeta$ chain and expressed the Fc$\epsilon\gamma$ chain normally not seen in T cells. The TCR in T cells from late TBM was therefore $\alpha\beta$, $\delta\epsilon$, Fc$\epsilon\gamma_2$ instead of the $\alpha\beta$, $\gamma\delta\epsilon\zeta_2$ seen in normal T lymphocytes. T lymphocytes from early TBM were not tested for TCR-CD3 structure.

Western blot analysis of T lymphocytes from late TBM revealed that $\zeta$ protein expression was undetectable in these cells. T lymphocytes from normal mice and early TBM, isolated under the same conditions, expressed normal levels of $\zeta$ protein. Thus, an important component in the TCR is absent from the TCR of T lymphocytes from late TBM. The loss of $\zeta$ protein expression in T lymphocytes from late TBM is correlated with the loss of in vitro cytotoxic and in vivo immunotherapeutic activity.

T lymphocytes from late TBM, however, produced normal levels of TCR. Western blotting with anti-Fc$\epsilon\gamma$ revealed the unique expression of this member of the $\zeta$ family in T lymphocytes from late TBM. The expression of Fc$\epsilon\gamma$ in T lymphocytes from late TBM may explain the presence in these cells of normal levels of TCR in their membrane.

EXAMPLE 10

Aberrant Signal Transduction in Lymphocytes from Late TBM

T lymphocytes from late TBM exhibit an altered form of signal transduction. This is evident from the fact that T lymphocytes from late TBM exhibit a significant decrease in their ability to mobilize Ca$^{2+}$ as compared to T lymphocytes from normal mice or late TBM. Calcium flux was measured in T lymphocytes by calcium sensitive fluorescence and the calcium concentration estimated *Current Protocols in Immunology*, Vol. I, J. E. Coligan, A. M. Kruisbeek, D. H. Margulies, E. M. Shevach and W. Strober (eds.), Green Publishing Associates and Wiley-Interscience, 5.5.1-5.5.15 (1991). Approximately $1 \times 10^7$ T cells were loaded with Indo 1 and stimulated with 10 μg/ml anti-CD3 MAb (145-2C11). Maximal flux was determined after lysis with calcium inophoore. Maximal fluorescence was determined after lysis with Triton-X 100 and minimum fluorescence after calcium chelation with EGTA.

Stimulation of lymphocytes from late TBM with anti-CD3 MAb revealed a significantly decreased ability to mobilize Ca$^{+2}$ as compared to those from normal mice or from early TBM. Even prolonged incubation with anti-CD3 (400 seconds) was not enough to achieve the levels of Ca$^{+2}$ flux seen in T cells from normal or early TBM. Stimulation of T lymphocytes from late TBM with calcium ionophore, however, resulted in equivalent maximum Ca$^{+2}$ flux demonstrating adequate intracellular stores in the cells.

Additionally, the pattern of phosphorylation of tyrosine residues in T lymphocytes from late TBM was markedly different compared to that of cells from normal mice or early TBM. Approximately 1×10; cells were estimulated in serum free medium with 10 μg/ml of anti-CD3 (145-2C11) for 2 minutes. The reaction was stopped by washing the cells twice in ice-cold phosphate-buffered saline containing 400 μM sodium orthovanadate and 1 mM EDTA. Cells were lysed in 100 μl of lysis buffer (25 mM Tris pH7.4, 150 mM NaCl, 0.5% Triton-X 100, 1 mM sodium orthovanadate, 10μg/ml aproptinin, 10 μg/m; leupeptin and 5 mM EDTA) for 5 min. on ice. Lysate were centrifuged and supernatants were analyzed by 10.5% SDS-PAGE under reduced conditions. Proteins were electrophoretically transferred onto PVDF filter (Imobilon-P), blocked with 5% gelatin in TBST buffer (20 mM Tris pH 7.4, 135 mM NaCl, 0.1% Tween 20) and incubated with anti-phosphotyrosine MAb (40 ng/ml). After washing, the blots were incubated with anti-mouse Ig MAb conjugated with peroxidase, subjected to ECL kit (Amersham) and exposed to an X-ray film.

The basal pattern of phosphorylated tyrosine residues was markedly altered in T lymphocytes from late TBM as compared to the other two groups. Changes in the residues in the 40–52 Mr range were consistently seen in three experiments. Stimulation with anti-CD3, however, induced the phosphorylation of tyrosine residues, demonstrating an effective signal transduction.

EXAMPLE 11

Expression of Lck is Undetectable in T Lymphocytes from Late TBM

Consistent with this altered pattern of phosphorylation in T lymphocytes from late TBM, the expression of Lck in these same cells was markedly decreased. The expression of Fyn, however, was unaltered. A sample cell lysate, prepared as described above, was run in an 8% SDS-PAGE and blotted with anti-Lck or anti-Fyn rabbit serum. The absence of ζ and the reduction in Lck may alter the signal transduction process, thereby preventing or delaying the activation of the lytic mechanism. Changes in the level of expression in T lymphocytes of ζ, CD3γ and Lck provide markers with which to identify cells capable of activation for adoptive immunotherapy.

EXAMPLE 12

Evaluation of Patients for Adaptive Immunotherapy

A patient having renal carcinoma is selected and a lymphocyte preparation is made from peripheral blood to be analyzed for the expression of ζ protein. Lymphocytes are obtained from a healthy individual and prepared and analyzed in the same manner. Peripheral blood lymphocytes are isolated by venipuncture or lymphapheresis. The cells are separated on a Ficoll-Hypaque gradient to obtain mononuclear cells. The cell density of the mononuclear cells thus obtained is determined and equal numbers of cells from the patient and the healthy individual are extracted for protein. Equal numbers of cells are solubilized in lysis buffer (25 mM Tris pH7.4, 150 mM NaCl, 0.5% Triton-X 100, 1 mM sodium orthovanadate, 10 μg/ml aproptinin, 10 μg/m; leupeptin and 5 mM EDTA). The lysate is centrifuged and the supernatant is immunoprecipitated with rabbit anti-normal rabbit serum. Immunoprecipitate is resolved by SDS-PAGE, transferred to Nylon membrane (Imobilon-P), and blotted with anti-ζ rabbit serum. A marked reduction in the expression ζ protein in the patient, as compared to the control, is diagnostic of immunosuppression and loss of the ability to use the patient's T lymphocytes in autologous adoptive immunotherapy.

What is claimed is:

1. A method of identifying patients having T lymphocytes capable of activation for autologous adoptive immunotherapy, comprising the steps of:
   a. directly determining, in a lymphocyte preparation from a patient being evaluated for immunosuppression, the level of expression of at least one selected TCR subunit protein or protein in the T lymphocyte signal transduction pathway, said protein being selected from the group consisting of ζ, CD3 γ, FCεγ, and Lck; and
   b. comparing said level of protein expression with the normal level of expression of said protein found in healthy individuals, and selecting patients whose level of expression of said protein is at or above the threshold level for response to activation for adoptive immunotherapy.

2. A method according to claim 1, wherein said level of expression is determined by determining the expression ration, wherein said expression ratio is the ratio of the number of T lymphocytes expressing said protein to the total number of T lymphocytes counted, said ratio being compared with the normal expression ratio found in healthy individuals.

3. A method according to claim 1, wherein said lymphocyte preparation is prepared from tissue or cells selected from the group consisting of spleen tissue, peripheral blood, tumor tissue, lymph node tissue, cerebrospinal fluid, pleural effusions and ascites.

4. In a method of treating patients having a disease responsive to autologous adoptive immunotherapy, wherein said patient is treated with stimulated T lymphocytes, the improvement wherein said patient is identified by a method according to claim 1.

5. A method according to claim 4, wherein said disease is cancer.

6. A method according to claim 5, wherein said level of expression is determined by determining the expression ratio, wherein said expression ratio is the ratio of the number of T lymphocytes expressing said protein to the total number of T lymphocytes counted, said ratio being compared with the normal expression ratio found in healthy individuals.

* * * * *